United States Patent [19]

Fujikura et al.

[11] Patent Number: 4,937,073
[45] Date of Patent: Jun. 26, 1990

[54] REFORMED VETIVER OIL AND VETIVEROL, PROCESS FOR PREPARING THE SAME, AND PERFUMERY COMPOSITION COMPRISING THE SAME

[75] Inventors: Yoshiaki Fujikura; Junji Koshino, both of Utsunomiya; Hiroaki Uchida, Ichikai; Manabu Fujita, Kashiwa; Nao Toi, Sakura, all of Japan

[73] Assignee: Kao Corporation, Tokyo, Japan

[21] Appl. No.: 302,246

[22] Filed: Jan. 27, 1989

[30] Foreign Application Priority Data

Jan. 28, 1988 [JP] Japan .................................. 63-18388
Jan. 29, 1988 [JP] Japan .................................. 63-19095
Feb. 15, 1988 [JP] Japan .................................. 63-32368

[51] Int. Cl.$^5$ .................... A61K 35/78; C11B 9/00; C11B 1/10
[52] U.S. Cl. ................................ 424/195.1; 512/5; 512/20; 512/22; 512/27
[58] Field of Search ................ 424/195.1; 512/5, 22, 512/20, 27

[56] References Cited

PUBLICATIONS

Chem. Abst. 76: 14740x, 1972.
Chem. Abst. 83: 197685u, 1975.
Chem. Abst. 68: 17099j, 1968.
Chem. Abst. 72: 55629v, 1970.

Primary Examiner—John W. Rollins
Attorney, Agent, or Firm—Oblon, Spivak, McClelland, Maier & Neustadt

[57] ABSTRACT

A reformed vetiverol comprising 40% by weight or more of khusimol and 10% by weight or less of isovalencenol is disclosed. The vetiverol, containing a small amount of isovalencenol and a large amount of khusimol imparts a milder and more elegant odor than conventional vetiver oils or vetiverols. The reformed vetiverol can be prepared by a process comprising: esterifying alcohol components in a vetiver oil or a vetiverol, heating the esterified vetiver oil or a vetiverol to thermally decompose isovalencenol esters, hydrolyzing the remaining esters into alcohols, and separating the formed alcohols.

1 Claim, No Drawings

REFORMED VETIVER OIL AND VETIVEROL, PROCESS FOR PREPARING THE SAME, AND PERFUMERY COMPOSITION COMPRISING THE SAME

BACKGROUND OF THE INVENTION

1. Field of the Invention

This invention relates to a reformed vetiver oil or vetiverol, and, more particularly, to a reformed vetiver oil or vetiverol having a smaller isovalencenol content and a greater khusimol content. The invention is also directed to a process for preparing such a reformed vetiver oil or vetiverol and to a perfumery composition containing the same.

2. Description of the Background

Vetiver oils are obtained by the steam-distillation of the roots of *Vetiveria zizanoides* belonging to the family of *Gramineae*. The oils are widely used for high-quality, expensive perfumery compositions and soap perfumes. Vetiver oils, however, have a harsh, woody odor inherent to plant roots. Eliminating this odor is essential to obtaining a high-quality perfumery material.

Generally known processes for preparing such perfumery materials are: (1) a process involving the fractional vacuum distillation of vetiver oil; (2) a process involving saponification of vetiver oil, followed by fractional vacuum distillation of the saponified material, and (3) a process comprising reacting vetiver oil and acetic anhydride to convert primary alcohol components into acetates, collecting the acetates by fractional distillation, and saponifying the collected acetate fractions to produce vetiver oil containing primary alcohols as major components. Alcohols contained in the vetiver oil produced by these processes are collectively called vetiverol. Vetiverol gives a warm, sweet, soily, balsamic, lasting fragrance, and is hence used as a high-quality, expensive perfumery material. In particular, the vetiverol produced by the above process (3) has the greatest primary alcohol content among the available vetiverols and is thus considered to be of the highest quality.

This process for producing the highest quality vetiverol, however, is not without some problems. Such problems are exemplified by (1) the difficulty in completely eliminating all alcohol components other than α-vetivone, β-vetivone, and primary alcohols by the fractional distillation of acetates; (2) the requirement of a rectification step which inevitably subjects the oil to heated conditions for a considerable period of time and tends to cause the oil to be heat-decomposed and deteriorated, producing a tar-like substance, which, in turn, reduces the yield of the target product; and (3) the necessity of expending great effort toward the elimination of an unfavorable, burning smell, and for the improvement of the odor after elimination of such a smell.

The chemical components which impart the fine fragrance of vetiver oils or vetiverols are still to be elucidated. There are very few published reports concerning the means for improving the fragrance of vetiver oils or vetiverols.

In view of this situation, the present inventors have undertaken extensive studies to produce a superior perfumery material from vetiver oils. In the course of this study, the inventors first isolated khusimol and isovalencenol which are the major components of vetiverols to evaluate their fragrance. As a result, the inventors have found that khusimol has a mild, long-lasting, powdery, warm, woody fragrance, and isovalencenol imparts a slightly oily, sandalwood-like fragrance. Furthermore, the inventors discovered that khusimol is a component giving a fragrance inherent to vetiver oils, which cannot be compared to any fragrances produced from any other materials. On the other hand, isovalencenol was found to have an excellent odor itself which is stronger than the odor of khusimol. The odor of isovalencenol, however, was found to act to offset the odor of khusimol inherent to vetiverol. In order to intensify the odor inherent to vetiverol and to further improve its fragrance, it is therefore necessary to selectively reduce the content of isovalencenol and to relatively increase the content of khusimol.

Khusimol and isovalencenol, however, are very similar to each other in their properties, which renders it difficult to separate them from each other using conventionally known refining methods. Only a very small amount can be isolated using gas chromatography, liquid chromatography, column chromatography, rectification, and other known techniques.

The inventors have carried out further studies to develop a process for the separation of khusimol and isovalencenol. As a result, the inventors have found that the primary alcohol components in vetiver oils could be very effectively converted into esters with an acid, especially with a dibasic acid anhydride and that these esters could be separated at a great efficiency to recover the primary alcohols by means of a simple treatment. In addition, the inventors have discovered that although both khusimol and isovalencenol were decomposed by heat or in the presence of a catalyst, the rate of the decomposition of isovalencenol esters was greater than that of khusimol esters, and further that isovalencenol contained in vetiver oils or vetiverols could be selectively decomposed through utilization of this difference of the decomposition rates between the two alcohols. The inventors' discoveries through these studies led to the possibility of eliminating isovalencenol with a high efficiency by a process comprising first esterifying the alcohol components contained in vetiver oils or vetiverols and then subjecting the resulting esters to thermal or catalytic decomposition for the selective removal of isovalencenol esters through the utilization of the difference of the decomposition rate of the two esters. The vetiverols thus prepared with a higher content of khusimol and a lower content of isovalencenol had a mild, elegant odor. Vetiver oils having a higher content of khusimol and a lower content of isovalencenol could produce vetiverols having an excellent odor. These findings have led to the completion of this invention.

SUMMARY OF THE INVENTION

Accordingly, an object of the present invention is to provide a reformed vetiverol comprising 40% by weight or more of khusimol and 10% by weight or less of isovalencenol (such a reformed vetiverol is hereinafter referred to as "reformed vetiverol A").

Another object of this invention is to provide a process for separating primary alcohols in a vetiver oil which comprises reacting a vetiver oil with an anhydrous dibasic acid to convert primary alcohol components in the vetiver oil into the dibasic acid half-esters, separating said half-esters from the reaction mixture, and hydrolyzing the separated half-esters (such separated primary alcohols in a vetiver oil is hereinafter referred to as "reformed vetiverol B").

Still another object of this invention is to provide a process for preparing a reformed vetiverol comprising 10% by weight or less of isovalencenol, comprising adding an acid having 1.0 to 3.0 pKa to a vetiver oil or a vetiverol, and heating the mixture to selectively decompose the isovalencenol contained in said vetiver oil or vetiverol (such a reformed vetiverol comprising 10% by weight or less of isovalencenol is hereinafter referred to as "reformed vetiverol C").

Other objects, features and advantages of the invention will hereinafter become more readily apparent from the following description.

DETAILED DESCRIPTION OF THE INVENTION AND PREFERRED EMBODIMENTS

It is essential that the reformed vetiverol A of this invention contain at least 40% by weight of khusimol and 10% by weight or less of isovalencenol. This is because a khusimol content of less than 40% by weight increases the relative content of isovalencenol, thus impairing the fragrance inherent to vetiver oils.

The reformed vetiverol A of this invention having the defined composition can be prepared, for example, by a process comprising esterifying alcohol components in a vetiver oil or a vetiverol, heating the esterified vetiver oil or a vetiverol to thermally decompose isovalencenol esters, hydrolyzing the residual esters into alcohols, and separating the formed alcohols.

There are no specific restrictions as to the types of acid used for the esterification. However, because of the requirement of a step for removing the components other than esters of primary alcohols, which follows the esterification of the primary alcohols and the selective thermal decomposition of isovalencenol esters, the selection of an acid which would produce a large boiling point difference between the primary alcohol esters and other components to be removed is desirable in view of economy. For this reason, desirable esterification agents are dibasic acid anhydrides or monobasic acid anhydride having a $C_5$ or more carbon atom content. Especially preferable acids are benzoic anhydride, succinic anhydride, maleic anhydride, phthalic anhydride, itaconic anhydride, citraconic anhydride, glutaric anhydride, and the like.

The esterification reaction may be carried out either in the presence or the absence of a catalyst. The temperature for the reaction, when carried out in the absence of a catalyst, is desirably between 80° to 160° C. Given as examples of the catalyst which can be used are orthophosphoric acid or alkali metal salts of the acid corresponding to the acid anhydride used in the esterification reaction. In the case where these catalysts are used, a preferable reaction temperature is in the range of from room temperature to 120° C.

The temperature for heat-decomposing isovalencenol esters depends on the types of acid used for the esterification or the types of esters produced. Usually, a desirable temperature is in the range of between about 130° to 200° C. For example, when the ester is a succinic acid half-ester, the temperature for the decomposition is between 140° and 180° C., and preferably between 150° and 170° C.

When the esterification temperature and heat-decomposition temperature are close to each other, there is no need to carry out the esterification and heat decomposition separately.

After the heat decomposition of isovalencenol esters, esters of alcohols other than isovalencenol esters are hydrolyzed. This hydrolysis can be carried out according to a conventional method using a base such as sodium hydroxide, potassium hydroxide, or the like. The reformed vetiverol A of this invention can be separated by the distillation under the reduced pressure of the reaction mixture obtained by the hydrolysis.

The reformed vetiverol A of this invention thus prepared may be formulated as a fragrance into perfumery compositions in an amount of 0.1 to 20% by weight to produce compositions having an excellent long-lasting odor.

In the above reaction, if a dibasic acid anhydride is used as an esterification agent, a reformed vetiverol B, i.e., primary alcohol components in vetiver oils, can be obtained through separation of primary alcohol half-esters from the esterification product, followed by hydrolysis of the half-esters.

More specifically, the product of the esterification reaction is subjected to simple distillation, molecular distillation, or Smith's distillation in vacuo to remove low-boiling point components and to obtain dibasic acid half-esters of primary alcohols as high-boiling point fractions. An alkali is then added to these high-boiling point fractions to effect hydrolysis and to produce target primary alcohol components in vetiver oil at a high purity. As an alkali, sodium hydroxide, potassium hydroxide, or the like can be used. Such an alkali may be added in the form of aqueous solution. There is no need to add a solvent, e.g. methanol, ethanol, or the like for solubilizing water and organic layers. Half-esters of primary alcohols have a surface activity enabling them to emulsify the system to which they are added. The reformed vetiverol B can easily be separated from the reaction mixture through vacuum distillation.

Reformed vetiverol C of this invention can be prepared as follows. An acid with a pKa of 1.0 to 3.0 is first added to a vetiver oil or a vetiverol and the mixture is heated. If the pKa of the acid is greater than 3, the acid and alcohols form esters, preventing the sufficient decomposition of the esters. On the other hand, if the pKa of the acid used is smaller than 1, the difference of the decomposition rate between khusimol and isovalencenol esters is too small to achieve selective decomposition of isovalencenol esters at a reasonable efficiency. Desirable acids meeting this criterion are, for example, citric acid, tartaric acid, succinic acid, phthalic acid, maleic acid, malonic acid, fumaric acid, nicotinic acid, iso-nicotinic acid, o-chlorobenzoic acid, chloroacetic acid, bromoacetic acid, fluoroacetic acid, 2-chloropropionic acid, and the like.

Although there are no specific restrictions as to the amount of acid to be added, a preferable amount is between 0.1 to 2 times the mol of isovalencenol. When a vetiver oil is used as a starting material, however, the amount of acid used may be 10 times the mole or greater of the amount of isovalencenol. A smaller amount of acid can be used, when a strong acid is used or a higher reaction temperature is employed.

The temperature to which the mixture is heated depends upon the types of acid used and upon whether a vetiver oil or a vetiverol is used as a starting material. From the aspect of assuring easy control of the reaction and of achieving high productivity, a temperature in the range of 50° to 180° C. is desirable.

A reformed vetiverol C thus prepared by selectively eliminating isovalencenol through decomposition has a 10% by weight or less isovalencenol content. The product can, therefore, be used as a perfumery material as is or after having been purified by means of vacuum distillation or the like means.

Reformed vetiver oils or vetiverols of this invention are useful as perfumery materials. Specifically, the reformed vetiverol B contains an extremely small amount of impurities and imparts a long-lasting, mild odor. This can be served as an exceptionally high-quality perfumery product. The reformed vetiverols A and C, especially the reformed vetiverol A, contain a small amount of isovalencenol and a large amount of khusimol. They give a milder and more elegant odor than conventional vetiver oils or vetiverols. These products, too, are useful as high-quality perfumery material. The perfumery compositions of this invention are, therefore, useful as a material for perfumery additives to be formulated into soaps and cosmetics.

Other features of the invention will become apparent in the course of the following description of the exemplary embodiments which are given for illustration of the invention and are not intended to be limiting thereof.

EXAMPLES

Example 1

Into a reaction vessel were charged 4 kg of a vetiver oil (originated in Java) and 514 g of succinic anhydride. The mixture was stirred at 120° C. for 4 hours under a nitrogen gas stream. The temperature was then raised to 160° C., at which temperature the mixture was stirred for a further 10 hours. After completion of the reaction, the resulting mixture was washed with water, and then submitted to vacuum distillation to remove 3,180 g of fractions having a boiling point lower than 140° C. at 0.15 mmHg. The residue amounting to 1,200 g was dissolved into 600 ml of hexane. To the resulting solution 600 ml of 25% NaOH aqueous solution was added and the mixture was stirred at room temperature for 5 hours. After completion of the reaction, the reaction mixture was washed with water. After removal of hexane and water by evaporation, the residue was submitted to vacuum distillation to collect fractions having a boiling point range of 104° to 112° C. at 0.15 mmHg. Analysis using capillary glass gas chromatography of the resulting vetiverol was as follows:

| | |
|---|---|
| Khusimol | 46.7% |
| Isovalencenol | 0.4% |
| Other primary alcohols | 52.3% |
| Ketones | 0.6% |

The reformed vetiverol A thus obtained gave a milder, more elegant fragrance than the conventional vetiverol (Composition: khusimol: 30.6%, isovalencenol: 25.9%, other primary alcohols and ketones: 43.5%).

Example 2

4 kg of a vetiver oil (originating in Java) and 1,162 g of benzoic anhydride were mixed and stirred at 120° C. for 6 hours under a nitrogen gas stream. The temperature was then raised to 170° C., at which temperature the mixture was stirred for a further 10 hours. After completion of the reaction, the resulting mixture was neutralized with an aqueous solution of sodium hydroxide, washed with water, and then submitted to vacuum distillation to remove 3,150 g of a fraction having a boiling point lower than 140° C. at 0.15 mmHg. The residue amounting 1,260 g was dissolved into 600 ml of n-hexane and 100 ml of methanol, and the solution was stirred at room temperature for 5 hours. After completion of the reaction, the reaction mixture was washed with water. After removal of hexane and water by evaporation, the residue was submitted to vacuum distillation to collect 560 g of fractions having boiling points of 104° to 112° C. at 0.15 mmHg. Analysis of this reformed vetiverol A thus prepared using capillary glass gas chromatography was as follows:

| | |
|---|---|
| Khusimol | 45.6% |
| Isovalencenol | 0.8% |
| Other primary alcohols | 53.0% |
| Ketones | 0.6% |

Example 3

4 kg of a vetiver oil (originating in Java) and 514 g of tartaric acid were mixed and the mixture was stirred at 120° C. for 4 hours under a nitrogen gas atmosphere.

After completion of the reaction, the resulting mixture was washed with water to remove the surplus succinic anhydride, and the residue was then submitted to vacuum distillation to remove about 2.52 kg of a fraction having a boiling point lower than 140° C. at 0.15 mmHg. The residue was further submitted to molecular distillation to remove 0.35 g of another low-boiling point fraction. To the residual high-boiling point fraction amounting to 1.45 kg, 600 ml of n-hexane and 600 ml of 25% NaOH aqueous solution were added, and the mixture was stirred at room temperature for 5 hours.

After completion of the reaction, the reaction mixture was washed with water, dried, and distilled in vacuo to produce a primary alcohol fraction (reformed vetiverol B) having a boiling point range of 104° to 115° C. at 0.15 mmHg. Analysis using capillary glass gas chromatography of the reformed vetiverol B was as follows:

| | |
|---|---|
| Khusimol | 38.2% |
| Isovalencenol | 17.0% |
| Other primary alcohols | 44.2% |
| Ketones | 0.6% |

Example 4

Into 50 g of vetiver oil (khushimol: 8.9%; isovalencenol: 3.9%; other components: 87.2%) 1.7 g of tartaric acid (pKa: 2.82; equivalent to about 130 mols of isovalencenol) was added and the mixture was reacted at 120° C. for 8 hours. Analysis of the reaction product (reformed vetiverol C) revealed khushimol content of 8% by weight (decomposition 10.1%) and isovalencenol contenst of 1.11% by weight (71.8% decomposition), thus evidencing selective decomposition of isovalencenol.

Example 5

The reaction was carried out under the same conditions as in Example 4, except that in place of tartaric acid other acids listed in the following table were used. The results are shown in the table.

| Acid | pKa | Reduced Rate (%) | |
|---|---|---|---|
| | | Isovalencenol | Khushimol |
| Citric acid | 2.87 | 77.6 | 39.9 |
| Nicotinic acid | 2.05 | 80.9 | 19.3 |
| Tartaric acid | 1.04 | 53.3 | 22.9 |

Example 6

Into 100 g of vetiverol (khusimol: 30.6%, isovalencenol: 25.9%, other primary alcohols: 43.5%) 3.57 g of tartaric acid (equivalent to 20% of isovalencenol) were added and the mixture was reacted at 120° C. for 10 hours. At this point, the isovalencenol content was confirmed to have reduced to as low as 4.1%. After cooling, a 5% sodium chloride aqueous solution and 200 ml of n-hexane were added to neutralize the mixture. The mixture was washed with water and dried over sodium sulfate anhydride. This dried material was submitted to fractional distillation in vacuo to collect the fraction having a boiling point range of between 106° to 114° C. at 0.15 mmHg to produce a reformed vetiverol C containing 39.1% khusimol. The product had a weak, but mild and elegant, woody odor characteristic to vetiver.

Example 7

Perfume for the preparation of *Eau de Cologne* <Formulation>

| <Formulation> | |
|---|---|
| Component | parts by weight |
| Bergamot oil | 100 |
| Lemon oil | 30 |
| Orange oil Guinea | 40 |
| Basil oil | 4 |
| Ylang Ylang oil extra | .50 |
| Jasmin base absolute type | 100 |
| Rose base | 50 |
| Rhodinol | 40 |
| Phenyl ethyl alcohol | 100 |
| Hydroxycitronellol | 30 |
| Methyldihydrojasmonate | 100 |
| Sandalwood oil mysore | 30 |
| Musk ketone | 20 |
| Cyclopentadecanolide | 50 |
| Amber base | 5 |
| Civet absolute | 1 |

750 parts by weight of the above perfumery composition and 250 parts by weight of reformed vetiverol A were mixed to give an *Eau de Cologne* preparation having an excellent lasting fragrance.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent is:

1. A reformed vetiver oil obtained by selectively removing isovalencenol from vetiver oil containing khusimol and isovalencenol such that the reformed vetiver oil has a khusimol content of 40% by weight or greater and an isovalencenol content of 10% by weight or less.

* * * * *